US00PP28056P3

(12) United States Plant Patent
Gray et al.

(10) Patent No.: US PP28,056 P3
(45) Date of Patent: May 30, 2017

(54) FLORIBUNDA ROSE PLANT NAMED 'GRASALM'

(50) Latin Name: ***Rosa* hybrid**
Varietal Denomination: GRAsalm

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 14/998,454

(22) Filed: Jan. 5, 2016

(65) Prior Publication Data

US 2016/0198604 P1 Jul. 7, 2016

(30) Foreign Application Priority Data

Jan. 7, 2015 (AU) ..... PBR 2015001

(51) Int. Cl.
*A01H 5/02* (2006.01)

(52) U.S. Cl.
USPC ..... Plt./147

(58) Field of Classification Search
USPC ..... Plt./147
CPC ..... A01H 5/0222
See application file for complete search history.

*Primary Examiner* — Kent L Bell

(57) ABSTRACT

'GRAsalm' is a new and distinct floribunda type *Rosa* hybrid cultivar which is characterized by the combination of an upright to semi-weeping growth habit, complete resistance to *Diplocarpon rosae*, nearly continuous flowering, double-type salmon flowers with tinges of apricot in hot weather, a strong rose fragrance, and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAsalm'.

CROSS REFERENCE TO RELATED APPLICATIONS

This application claims priority to the Australian Plant Breeder's Rights application number 2015001, filed on Jan. 7, 2015, which is herein incorporated by reference.

BACKGROUND OF THE INVENTION

The present invention relates to a new and distinct *Rosa* hybrid, floribunda rose cultivar, which has been given the variety denomination of 'GRAsalm'.

Parentage: 'GRAsalm' is a seedling selection which resulted from the controlled cross-pollination of an unnamed *Rosa* hybrid female breeding line and an unnamed *Rosa* hybrid male breeding line. Both parents, developed by the same inventor and never commercially released, exhibited traits deemed commercially significant and desirable.

After many years of trialing, the female parent was confirmed to possess a combination of desirable traits such as complete resistance to rose black spot disease, complete resistance to powdery mildew, and flowers with a strong citrus-like perfume borne on a bushy plant growing to 1.2 m tall and wide. The male parent was selected for use in breeding after trialing confirmed the presence of strong true-rose perfume and a bright, modern flower color. During the summer of 2010, the female parent was emasculated and was manually pollinated with pollen from the male parent. In autumn of 2010, seed was collected from hips produced by the female parent and a number of seedlings were grown to a mature size, including the claimed plant. These progeny were further evaluated for desirable traits such as black spot disease resistance and strong perfume, and in June of 2011 the claimed plant was first observed. In January of 2013, after further evaluation for desirable traits, the claimed plant was deemed to be garden-worthy and suited to widespread cultivation. It was given the denomination, 'GRAsalm'.

Asexual Reproduction: Asexual propagation of 'GRAsalm', by way of softwood stem cuttings, was first performed in May of 2011 at the inventor's nursery in Highfields, Australia. Through greater than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAsalm'. These traits, in combination, distinguish 'GRAsalm' as a new and distinct cultivar.

1. *Rosa* hybrid 'GRAsalm' exhibits an upright to semi-weeping growth habit; and
2. *Rosa* hybrid 'GRAsalm' exhibits complete resistance to the plant pathogen, *Diplocarpon rosae*, commonly referred to as rose black spot disease; and
3. *Rosa* hybrid 'GRAsalm' exhibits nearly continuous flowering; and
4. *Rosa* hybrid 'GRAsalm' exhibits a double flower type; and
5. *Rosa* hybrid 'GRAsalm' exhibits salmon colored flowers, with tinges of apricot in hot weather; and 6. *Rosa* hybrid 'GRAsalm' exhibits flowers with a strong rose fragrance.

DETAILED BOTANICAL DESCRIPTION

Figure 1:
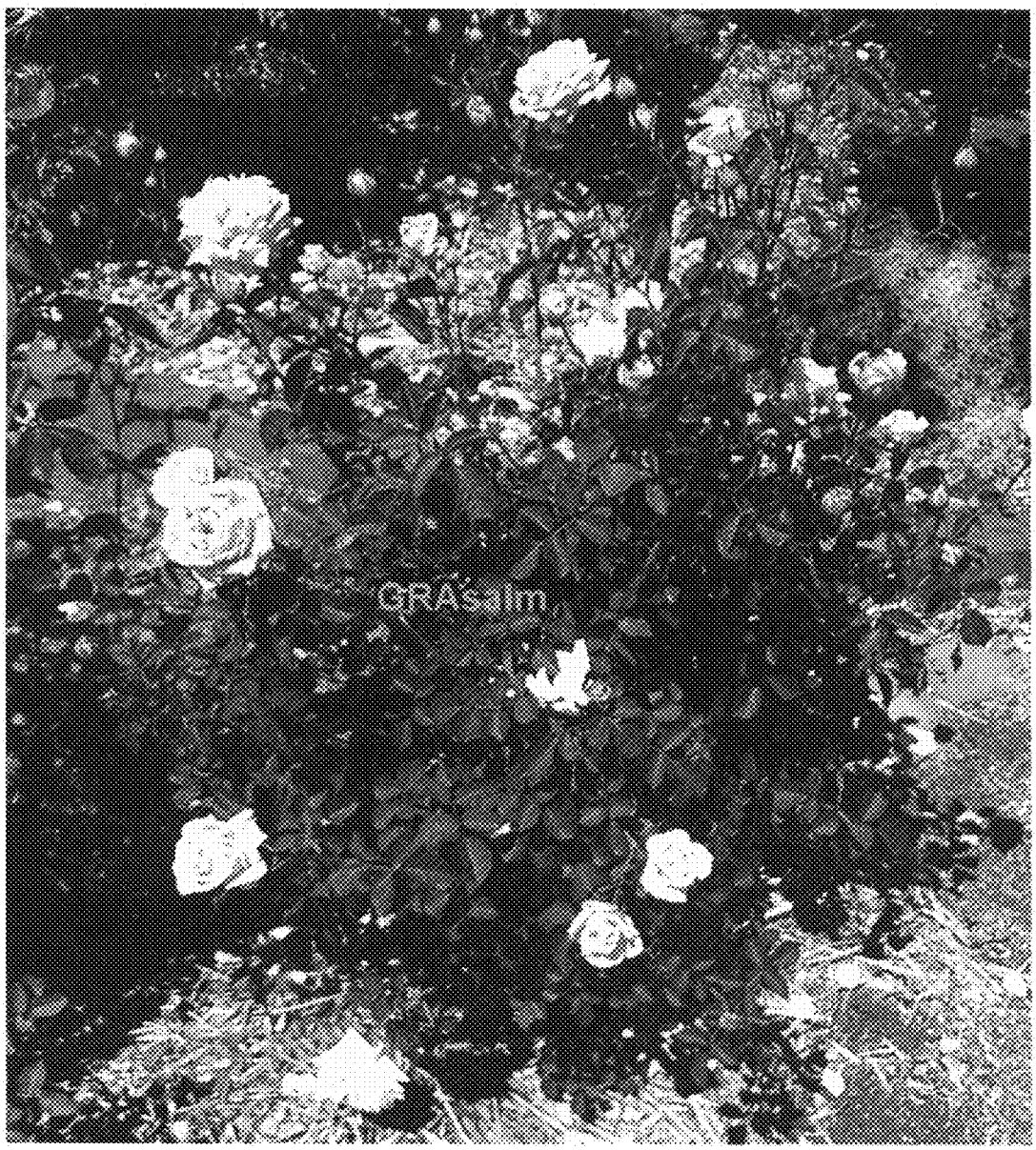
FIG. 1 illustrates, as nearly true as it is reasonably possible to make the same in color photographs of this type, an exemplary 2 year old 'GRAsalm' plant grown outdoors at the inventor's commercial nursery in Highfields, Australia.
Figure 2:
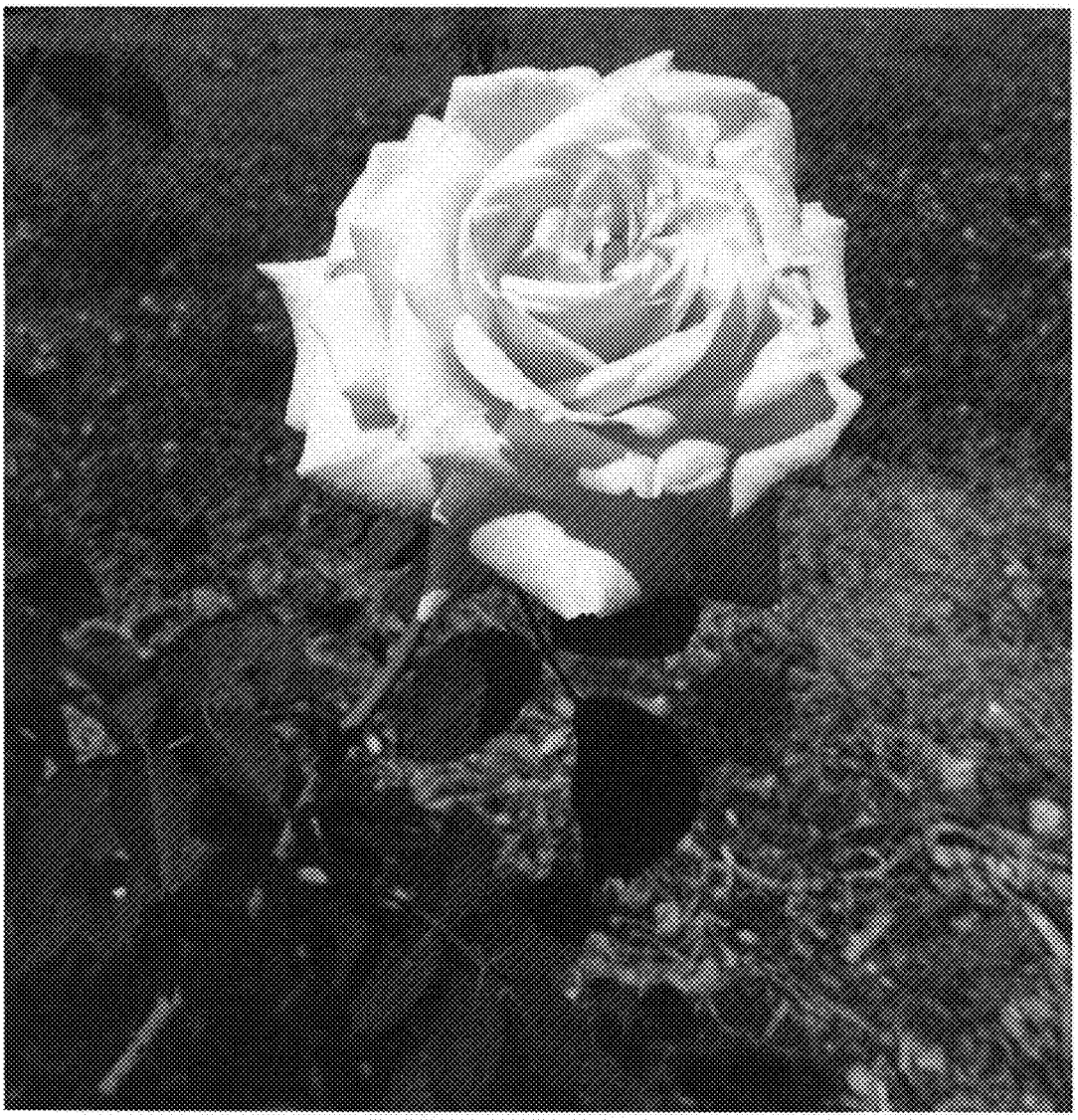
FIG. 2 illustrates, as nearly true as it is reasonably possible to make the same in color photographs of this type, the typical foliage and flower of 'GRAsalm'.

The following observations and measurements, made in November of 2015, describe averages of two specimens of two year old 'GRAsalm' plants grown in red krasnozem soil, in full sun, at the inventor's nursery in Highfields, Australia. Temperatures ranged from approximately 12 to 35 degrees Celsius during the day and 3 to 18 degrees Celsius at night. Standard practices for irrigation, fertilizer and pest control were applied at appropriate times during the growing season. The plants were pruned in July of 2015 using accepted techniques for rose pruning.

Those skilled in the art will appreciate that certain characteristics will vary with older or, conversely, with younger plants. 'GRAsalm' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2007 Fifth Edition except where common terms of color are used.

A botanical description of 'GRAsalm' and comparisons with the parents and the most similar commercial cultivar of *Rosa* hybrid are provided below.

General plant description:

*Growth habit*.—Upright to semi-weeping.

*Growth rate*.—Approximately 1 years to reach 100 cm.

*Mature dimensions*.—110 cm tall and 90 cm wide.

*Cold hardiness*.—Unknown.

*Disease resistance*.—Complete resistance to powdery mildew (*Sphaerotheca pannosa*) and blackspot (*Diplocarpon rosae*).

Propagation:

*Technique*.—Softwood stem cuttings.

*Time to initiate roots*.—About 13 days at approximately 22 degrees Celsius ambient temperature.

*Time to produce a rooted cutting*.—About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit*.—Irregular branching from mature branches, breaking first from the uppermost buds near the apex of each shoot.

*Quantity*.—Numerous.

*General dimensions*.—Approximately 40 to 60 cm long; 0.5 cm in diameter near the base and tapering to 0.3 cm.

*Immature branches*.—Diameter — Approximately 0.3 cm. Texture — Smooth; glabrous to moderately pubescent. Color — Near RHS 145C. Prickles — Density — Many. Color — Near RHS 39A. Shape — Deltoid. Texture — Smooth.

*Mature branches*.—Diameter — Approximately 1 cm, after 2 years. Texture — Smooth; glabrous. Color — Near RHS 145B. Prickles — Density — Many. Color — Near RHS 39A. Shape — Deltoid. Texture — Smooth.

Leaves:

*Arrangement*.—Alternate imparipinnate compound leaves.

*Attachment*.—Petiolate.

*Dimensions*.—11 cm long and 7 cm wide, on average.

Petiole:

*Dimensions*.—Average of 1.5 to 2.2 cm long and 0.2 cm wide.

*Color*.—RHS 145C.

*Texture*.—Glabrous to lightly pubescent with few small hairs.

*Prickles*.—Not present.

*Stipitate glands*.—Not present.

Stipule:

*Dimensions*.—1.2 cm long and 0.6 cm wide.

*Color*.—Near RHS 145C.

*Texture*.—Glabrous to lightly pubescent with few small hairs.

*Margins*.—Ciliate.

*Apex*.—Acuminate.

*Base*.—Fused to the petiole.

*Prickles*.—Present

*Stipitate glands*.—Not present.

Rachis:

*Dimensions*.—1.7 cm long and 0.2 cm wide.

*Color*.—Near 135D.

*Prickles*.—Present.

*Stipitate glands*.—Not present.

Leaflets:

*Quantity*.—Normally 7 leaflets on axillary leaves.

*Dimensions*.—Average size of the terminal leaflet is 4 cm long and 3 mm wide.

*Shape*.—Ovate.

*Apex*.—Acuminate.

*Base*.—Rounded to cordate.

*Margins*.—Serrated.

*Texture, pubescence and luster, adaxial surface*.—Smooth, glabrous, and semi-glossy.

*Texture, pubescence and luster, abaxial surface*.—Smooth, glabrous, and matte.

*Juvenile foliage color, adaxial surface*.—Near RHS 149C, with some anthocyanin intonations, RHS 46A, at the margins.

*Juvenile foliage color, abaxial surface*.—Near RHS 149D, with some anthocyanin intonations, RHS 42C, at the margins.

*Mature foliage color, adaxial surface*.—Near RHS 139B.

*Mature foliage color, abaxial surface*.—Near RHS 138B.

*Venation*.—Reticulate.

*Venation color, adaxial surface*.—Near RHS 139B.

*Venation color, abaxial surface*.—Near RHS 140D.

*Petiolule*.—Dimensions — 0.2 cm long and 0.1 cm wide. Color — Near RHS 135D. Prickles — Not present. Texture — Smooth.

Inflorescence:

*Inflorescence type*.—Terminal corymb consisting of approximately 1 to 6 pedicellate flowers.

*Blooming habit*.—Almost continuous from October through June in the southern hemisphere.

*Time to flower*.—6 to 8 weeks for a new stem to mature and flowering begins to occur once a stem matures.

*Dimensions*.—18 cm from the base of the base of the lowest pedicel to the farthest distal flower and 20 cm from farthest outstretched flower on one side of the inflorescence to the farthest outstretched flower on the opposite side.

Peduncle:

*Dimensions*.—14 cm long and 0.4 cm in diameter.

*Color*.—Near RHS 149A.

*Strength*.—Strong.

*Texture*.—Prickles present.

Bud:

*Bud form*.—Ovate.

*Size*.—2 cm long and 2 cm in diameter.

*Color*.—Near RHS 143C.

Flower:

*Pedicel*.—Dimensions — 5 to 6 cm long and 0.3 cm wide. Color — Near RHS 151D. Strength — Strong. Texture — Slightly pubescent; small hairs present.

*Calyx*.—General — Comprised of five polysepalous sepals, with medium foliaceous appendages present on all sepals. Diameter of calyx — 0.8 cm. Sepals — Color, interior surface — RHS 145D. Color, exterior surface — RHS 143C. Dimensions — 2.5 cm long and 0.8 cm wide. Apex — Acuminate. Base — Flat at union with receptacle. Quantity — Five. Texture — Soft and slightly felted. Margins — Two to three weak foliaceous appendages. Stipitate glands — Not present.

Corolla:

*General shape of corolla*.—Double; round.

*Rate of opening*.—10 days from bud to anthesis.

*Dimensions*.—8 to 10 cm in diameter and 3.6 cm deep.

*Upper profile*.—Flattened convex.

*Lower profile*.—Flat.

*Fragrance*.—Strong rose scent.

*Lastingness*.—On the plant for 5 days after anthesis.

*Persistence*.—Self-cleaning.

Petals:

*Petal count*.—Exhibits double flowers with approximately 30 petals under normal conditions.

*Petal arrangement*.—Tight whorl.

*Petal reflex*.—Medium reflexing on outer petals.

*Petal margin*.—Entire; slightly undulating.

*Petal shape*.—Rounded.

*Apex*.—Rounded.

*Base*.—Obtuse.

*Dimensions*.—4.0 cm long and 3.6 cm wide.

*Texture*.—Soft.

*Petal color, upon opening*.—Upper surface — Near RHS 56C. Lower surface — Near RHS 49A.

*Petal color, at anthesis*.—Upper surface — Near RHS 49D in spring and changing to near RHS 22D in early summer. Lower surface — Near RHS 48D in spring and changing to near RHS 24D in early summer. Fading — Salmon pink, RHS 36A, to pale pink, near RHS 36D.

Reproductive organs:

*Stamens*.—Quantity — Approximately 100. Anthers — Shape — Narrow ovate. Length — 0.1 cm. Color — Near RHS 169C. Pollen — Many. Pollen Color — RHS 23A. Filaments — Color — RHS 43C. Length — Approximately 2 cm.

*Pistils*.—Quantity — Approximately 50. Length — Approximately 0.8 cm. Stigmas — Shape — Rounded. Color — Near RHS 18B. Styles — Length — Approximately 0.4 cm long. Color — Near RHS 60A.

*Ovary*.—Dimensions — 0.5 cm long and 0.3 cm wide. Color — Near RHS 3D.

*Receptacle*.—Shape — Pitcher-shaped. Dimensions — 0.6 cm high and 0.6 cm wide. Color — RHS 130D.

Hip and seed:

*Hip*.—

*Shape*.—Rounded.

*Dimensions*.—1 cm long and 1 cm wide.

*Texture*.—Smooth.

*Color*.—Near RHS 150D.

Seed: Not observed.

COMPARISONS WITH THE PARENTS

The new rose plant 'GRAsalm' may be distinguished from its seed parent, an unnamed breeding line, by the following combination of characteristics:

1. The flowers of 'GRAsalm' exhibit a salmon general tonality with tinges of apricot in hot weather, whereas the flowers of the seed parent exhibit a soft pink general tonality.
2. 'GRAsalm' exhibits juvenile foliage with heavy anthocyanin intonations, whereas the juvenile foliage of the seed parent lacks anthocyanin intonations.

The new rose plant 'GRAsalm' may be distinguished from its pollen parent, an unnamed breeding line, by the following combination of characteristics:

1. The flowers of 'GRAsalm' exhibit a salmon general tonality with tinges of apricot in hot weather, whereas the flowers of the pollen parent exhibit a purple general tonality.
2. 'GRAsalm' exhibits glossy dark green mature foliage, whereas the pollen parent exhibits matte blue-green mature foliage.

COMPARISONS WITH THE MOST SIMILAR VARIETY OF COMMON KNOWLEDGE

Plants of the new cultivar 'GRAsalm' may be distinguished from the commercial variety *Rosa* hybrid 'GRAppl' (U.S. patent application Ser. No. 14/120,562) by the following combination of characteristics:

1. The flowers of 'GRAsalm' exhibit a salmon-pink to apricot general tonality, whereas the flowers of 'GRAppl' exhibit a purple general tonality.
2. 'GRAsalm' exhibits a petal count of approximately 30 petals, whereas 'GRAppl' typically possesses 22 petals.
3. 'GRAsalm' exhibits average leaf dimensions of 11 cm long and 7 cm wide, whereas 'GRAppl' exhibits average leaf dimensions of 13.5 cm long and 8.5 cm wide.
4. 'GRAsalm' exhibits average bud dimensions of 2 cm long and 2 cm wide, whereas 'GRAppl' exhibits average bud dimensions of 3.3 cm long and 1.8 cm wide.

That which is claimed:

1. A new and distinct variety of *Rosa* hybrid plant named 'GRAsalm', as described and illustrated herein.

* * * * *